Figure 1:
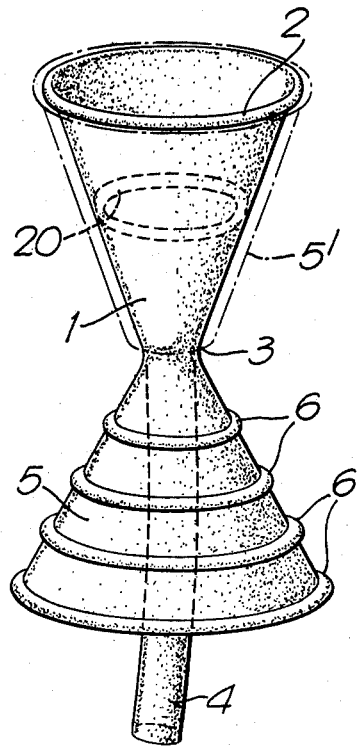

United States Patent [19]

Heimreid

[11] 4,388,923
[45] Jun. 21, 1983

[54] EXTERNAL URINARY DRAINAGE DEVICE

[76] Inventor: Ken Heimreid, Brananvein 44B, Heistad, Norway

[21] Appl. No.: 257,614

[22] Filed: Apr. 27, 1981

[30] Foreign Application Priority Data

May 13, 1980 [NO] Norway ................................. 801426

[51] Int. Cl.³ .............................................. A61F 5/44
[52] U.S. Cl. ..................................... 604/352; 128/767
[58] Field of Search ................. 128/79, 132, 157, 294, 128/295, 767, 138 R, 760, 767; 604/349, 351, 352

[56] References Cited

U.S. PATENT DOCUMENTS

| 480,911 | 8/1892 | Vance | 128/294 |
| 3,863,638 | 2/1975 | Rogers et al. | 128/295 |
| 4,239,044 | 12/1980 | Pavlinch | 128/295 |
| 4,320,752 | 3/1982 | Comparetto | 128/294 |

FOREIGN PATENT DOCUMENTS 554178 2/1932 Fed. Rep. of Germany ........ 128/79

Primary Examiner—Richard J. Apley
Assistant Examiner—J. L. Kruter
Attorney, Agent, or Firm—Cushman, Darby & Cushman

[57] ABSTRACT

An external urinary drainage means in the form of a condom which at the outer end thereof terminates in or is connected to a length of hose for carrying off the urine. The condom is formed as a short condom which covers only the head (glans) of the penis. Extending from the outer end of the condom or from the length of hose is a sheathing body which, when the condom surrounds the head of the penis and the foreskin has been drawn forward over the condom, can be made to encase the condom and foreskin, thereby providing a labyrinth seal. At the inner edge of the condom, a recessed section can be provided to accomodate the neck of the penis at the corona. The sheathing body is tightly connected to the outer end of the condom or to the length of hose, preferably such that a space is formed between the length of hose, the condom and the sheathing body.

9 Claims, 6 Drawing Figures

U.S. Patent Jun. 21, 1983 Sheet 1 of 2 4,388,923

EXTERNAL URINARY DRAINAGE DEVICE

The invention pertains to an urinary drainage means in the form of a condom which at one outer end thereof terminates in or is connected to a length of hose for carrying off the urine, the condom being formed so as to cover only the head (glans) of the penis.

For male patients who lack control over urination, whether they are bedridden or ambulatory, one has to rely on the use of diapers or sanitary napkins, catheters or an external urinary drainage means in the form of a condom which is connected to a hose for transferring the urine to a container, which the patient optionally can carry around with him. The use of diapers and the like is unpleasant, can easily lead to the formation of sores, restricts movement for ambulatory patients, and is also expensive. The use of catheters is very unpleasant and may often be painful, and can in addition be a source of infection and other bodily reactions. A condom with a connected hose is, as far as it goes, an elegant solution to a difficult problem, but has the drawbacks that it can fall off, often without the patient being aware of it, and especially in the case of bedridden patients, the urine has a tendency to seep out between the penis and the condom wall, with unpleasant consequences.

An external urinary drainage means of the type defined introductorily is known from German Pat. No. 520.401. The condom is preferably held in place by pulling the foreskin forward over the condom and placing a retainer band around the foreskin to press it against the condom.

The aim of the invention is to provide an external urinary drainage means of the condom type which not only stays securely in place but also provides an improved and more reliable seal than the types in use today. Using the known embodiments as a point of departure, then, it is proposed according to the invention that the condom be formed such that it covers only the head of the penis and sits there during use, while at the same time the foreskin acts as a sealing or labyrinth member. When the short condom has been positioned on the head of the penis, the foreskin is pulled forward over the condom, and a separate sheathlike body, tightly connected to the condom or to the length of hose, is then drawn over the condom and foreskin, thus providing a labyrinth seal.

Thus, according to the invention an external urinary drainage means is provided in the form of a condom which at one outer end terminates in or is connected to a length of hose for transferring the urine, the condom being formed so as to cover only the head (glans) of the penis, and that which characterizes the invention is that extending from the outer end of the condom is a sheathing body which is tightly connected to the condom or to the length of hose and which, after the condom has been positioned so as to cover the head of the penis and the foreskin drawn forward over the condom, can be made to encase the condom and foreskin.

The external urinary drainage means can be made of a soft and elastic material, as in conventional condoms, but can also utilize a more or less rigid material for the condom itself, which then becomes more like a cup, while the sheathing body must have the property of being able to be pulled over the condom and foreskin and lie against the foreskin with a certain elastic tension, for provision of the desired sealing effect.

Preferably, the condom is provided with an inwardly-projecting marginal bead or flange for engagement in back of the head of the penis, such that one thereby ensures good retention of the condom on the head of the penis.

The new external urinary drainage means can naturally be produced in several sizes; preferably, however, the condom is provided with an additional inwardly-projecting annular bead or flange spaced a distance interior of the said marginal bead and having a smaller aperture than the latter. Thus, one can easily adjust the size of the condom as required by cutting the condom just outside the inner annular bead, such that the latter becomes a marginal bead.

The sheathing body is preferably formed as a body which projects outwardly from the outer end section of the condom and which can be rolled or folded back toward the opposite, bead end of the condom. This makes it easier to put the device on the patient.

Preferably, the sheathing body also has one or more annular beads or ribs intended for contact against the foreskin, and optionally against the annular region in back of the head of the penis.

Preferably, space is provided between the outer end of the condom and the sheathing body for containing the forward part of the foreskin. This is especially desirable for patients with large foreskins. A practical way of providing such space is that the location at which the sheathing body is tightly connected to the length of hose can be spaced a distance from the outer end of the condom.

The sheathing body can either be permanently attached to or detachable from the length of hose, the essential point being that a sufficiently tight connection is ensured.

It may be advantageous to provide the inner edge of the condom with a recessed section to accommodate the so-called neck of the penis at the corona, in order to avoid pinching in this area.

Figure 2:
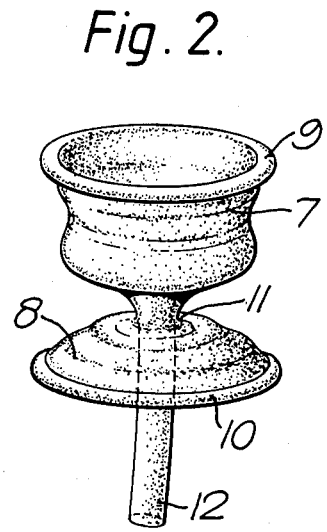
Figure 3:
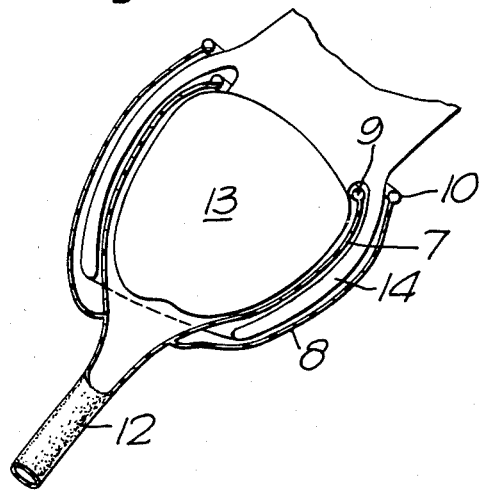
Figure 4:
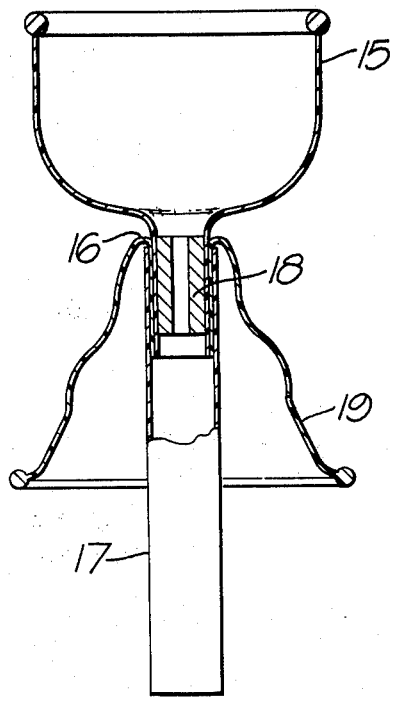
Figure 5:
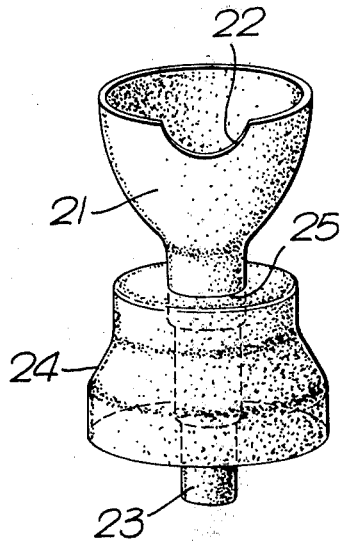
Figure 6:
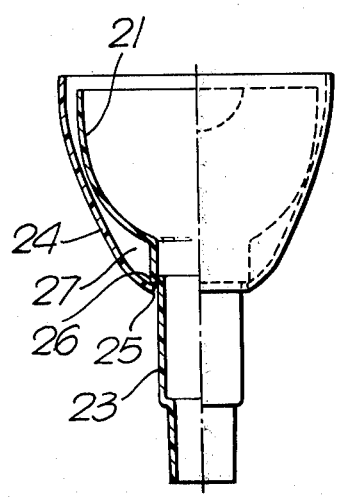

The invention will be elucidated in greater detail in the following with reference to the accompanying drawings, wherein:

FIG. 1 shows, in perspective view, an external urinary drainage means according to the invention, FIG. 2 shows, also in perspective, a second possible embodiment of an external urinary draining means in accordance with the invention, FIG. 3 shows the device of FIG. 2 in cross section and in position on the head of a penis, FIG. 4 is a cross section through a modified embodiment of the device of FIG. 2, FIG. 5 shows, in perspective view, another modified embodiment of the invention, and FIG. 6 shows the embodiment of FIG. 5 in partial cross section.

The external urinary drainage means shown in FIG. 1 is formed with a short condom 1, here in the form of a semi-rigid funnel which at the mouth of the funnel is provided with an inwardly-projecting marginal bead 2 intended for engagement in back of the head of the penis, and at the opposite, outer end 3 terminates in a tube or length of hose for conducting urine from the inside of the condom or cup 1. Also extending outwardly from the outer end section 3 of the condom is a sheathing body 5 which is capable of being rolled back or reversed. The sheathing body is also funnel-shaped and can be rolled back or reversed into the position indicated by the dashed lines in the drawing, designated by reference number 5'. On the surface which faces inwardly when the sheath has been rolled back, the sheathing body has several circumferential beads 6 which are intended for contact against the foreskin when the sheath has been reversed into the position 5.

The embodiment illustrated in FIG. 2 is in principle formed in the same way as the embodiment of FIG. 1, but the condom 7 itself is in this case made of a conventional, soft elastic material, and the same is true of a sheathing body 8. Both the condom 7 and the sheath 8 have marginal beads, 9 and 10 respectively. At the outer end section 11 of the condom 7, from which the sheathing body 8 extends, the condom 7 is connected to a length of hose 12 for conducting the urine.

FIG. 3 shows the external urinary drainage means of FIG. 2 in position on the head of the penis 13. The condom itself 7 is first placed on the head of the penis 13, with the marginal bead 9 positioned in back of the head of the penis. The foreskin 14 is drawn forward over the condom 7, and the sheathing body 8 is then drawn backwards over the foreskin and head of the penis. The external urinary drainage means is thereby securely positioned in a sealed manner.

In both FIG. 1 and 2, the respective lengths of hose, 4 and 12, are integral with the condom itself, 1 and 7, respectively. FIG. 4 shows a modified embodiment in which a condom 15, corresponding to the condom 7, has an outer end section 16 which is inserted into a separate length of hose 17 and retained therein by means of an inserted tube 18. The length of hose 17 is integral with a sheathing body 19, capable of being folded back on itself or reversed, which corresponds to the sheath 8 in FIG. 2.

The embodiment illustrated in FIG. 1 has an extra internal annular bead 20 arranged a suitable distance interior of the marginal bead 2. The annular bead 20 has a smaller aperture than the marginal bead 2. By cutting the condom 1 immediately in back of the annular bead 20, one can obtain a smaller condom suitable, for example, for fitting to a younger male patient.

Tests have shown that the new external urinary drainage means stays in place well and shows no tendency to fall off or loosen. The labyrinth seal provided as a result of the foreskin's being drawn forward over the condom and being covered in turn by the sheathing body provides a very effective seal, and the problem of urine leakage, which is especially a problem with bedridden patients, is in practice eliminated with the new external urinary drainage means.

The embodiment illustrated in FIGS. 5 and 6 is distinguished by a recessed section 22 at the inner edge of the condom 21, adapted to accommodate the neck of the penis at the corona. The condom 21 is integral with a length of hose 23, and a reversible sheathing body 24 is threaded onto the hose 23. In FIG. 5, the sheathing body is shown turned down, preparatory to positioning the external urinary drainage means on the head of a penis (not shown), while in FIG. 6 the sheathing body has been reversed and turned up into the position it assumes during use of the device. The sheathing body 24 has an opening 25 at the bottom through which the length of hose 23 is inserted. The elasticity of the materials ensures a sufficiently tight connection between the length of hose and the edge of the opening at the bottom of the sheath. In the transition between the condom and the hose, an external annular shoulder 26 is formed, which forms a stop edge for the sheathing body 24 at a distance spaced from the outer end of the condom, such that a space 27 is provided for containing the forward portion of the foreskin (which is not shown in the drawing).

The term "condom" as used above and in the claims is not restrictive and is meant to cover all adaptable receptacle-like embodiments which may be used within the inventive concept.

Having described my invention, I claim:

1. In an external urinary drainage device which includes a condom having an open rearward end and a forward end in sealed communication with a length of hose for transferring the urine, the condom having a length and shape such as to cover only the head (glans) of the penis, the improvement comprising a funnel shaped sheathing body means coaxial with the condom and sealing connected around the periphery of the condom adjacent the forward end thereof and so located that, when the condom surrounds the head of the penis and the foreskin has been drawn forward over the condom, the sheathing body means can be reversed to encase the condom and foreskin.

2. An external urinary drainage means according to claim 1, characterized in that the condom has an inwardly-projecting marginal bead for engagement in back of the head of the penis.

3. An external urinary drainage means according to claim 2, characterized in that the condom has an additional inwardly-projecting annular bead spaced a distance interior of the said marginal bead and having a smaller aperture than the latter.

4. An external urinary drainage means according to claim 1, characterized in that the sheathing body means is formed as a body which extends outwardly from the outer end section of the condom and which can be rolled back.

5. An external urinary drainage means according to claim 1, characterized in that the sheathing body means has at least one circumferential beads intended for contact against the foreskin.

6. An external urinary drainage means according to claim 1, characterized in that the condom is formed as a semi-rigid cup.

7. An external urinary drainage means according to claim 1, characterized in that the sheathing body means is tightly connected to the length of hose at a distance spaced from the outer end of the condom such that a space is provided between the length of hose, the condom and the sheathing body.

8. An external urinary drainage means according to claim 1, characterized in that the sheathing body means is formed as a separate body having an opening at the bottom through which the length of hose is inserted.

9. An external urinary drainage means according to claim 1, characterized in that there is provided a recessed section at the inner edge of the condom, adapted to accommodate the so-called neck of the penis at the corona.

* * * * *